(12) United States Patent
Barmat et al.

(10) Patent No.: US 10,907,132 B2
(45) Date of Patent: Feb. 2, 2021

(54) SCAFFOLDS FOR UTERINE CELL GROWTH

(71) Applicant: Lehigh University, Bethlehem, PA (US)

(72) Inventors: Larry Barmat, Abington, PA (US); Matthias Falk, Emmaus, PA (US); Himanshu Jain, Bethlehem, PA (US); Stephen Somkuti, Abington, PA (US)

(73) Assignee: Lehigh University, Bethlehem, PA (US)

( * ) Notice: Subject to any disclaimer, the term of this patent is extended or adjusted under 35 U.S.C. 154(b) by 450 days.

(21) Appl. No.: 15/784,917

(22) Filed: Oct. 16, 2017

(65) Prior Publication Data
US 2018/0105799 A1 Apr. 19, 2018

Related U.S. Application Data

(60) Provisional application No. 62/408,407, filed on Oct. 14, 2016.

(51) Int. Cl.
| | | |
|---|---|---|
| *C12N 5/071* | (2010.01) | |
| *A61F 2/00* | (2006.01) | |
| *A61B 17/435* | (2006.01) | |

(52) U.S. Cl.
CPC .......... *C12N 5/0682* (2013.01); *A61B 17/435* (2013.01); *A61F 2/0063* (2013.01); *A61F 2002/0086* (2013.01); *C12N 2500/60* (2013.01); *C12N 2502/02* (2013.01); *C12N 2509/00* (2013.01); *C12N 2533/12* (2013.01); *C12N 2535/00* (2013.01)

(58) Field of Classification Search
CPC .............. C12N 5/0682; C12N 2535/00; C12N 2500/60; C12N 2509/00; C12N 2502/02; C12N 2533/12; A61F 2/0063; A61F 2002/0086; A61B 17/435
See application file for complete search history.

(56) References Cited

U.S. PATENT DOCUMENTS

| | | | |
|---|---|---|---|
| 8,277,829 | B2 | 10/2012 | Jain |
| 8,389,018 | B2 | 3/2013 | Jain |
| 9,321,675 | B2 | 4/2016 | Jain |
| 9,656,900 | B2 | 5/2017 | Jain |
| 9,701,566 | B2 | 7/2017 | Moawad |
| 2003/0206928 | A1* | 11/2003 | Tormala ................ A61L 31/128 424/400 |

(Continued)

OTHER PUBLICATIONS

Kimura et al. "On-Chip Single Embryo Coculture with Microporous-Membrane-Supported Endometrial Cells" IEEE Transactions on Nanobioscience, vol. 8, No. 4, pp. 318-324 (Year: 2009).*

(Continued)

*Primary Examiner* — Kaylee R Wilson
(74) *Attorney, Agent, or Firm* — FisherBroyles, LLP

(57) ABSTRACT

A method for growing polarized endometrial cells, said method comprising: (a) disposing endometrial cells on a scaffold, said scaffold comprising a silica-based glass composition, characterized by multi-modal porosity, said scaffold being to define a top side and a bottom side; (b) providing nutrients to said top and bottom sides of said scaffold and an environment to grow polarized endometrial cells on said scaffold.

21 Claims, 2 Drawing Sheets

(56) References Cited

U.S. PATENT DOCUMENTS

| | | | |
|---|---|---|---|
| 2010/0015244 A1* | 1/2010 | Jain | A61L 27/10 424/602 |
| 2014/0075993 A1* | 3/2014 | Jain | C03C 11/00 65/17.2 |

OTHER PUBLICATIONS

Yao et al. "Bioglass/chitosan-polycaprolactone bilayered composite scaffolds intended for osteochondral tissue engineering" Journal of Biomedical Materials Research, vol. 102A, Issue 12, pp. 4510-4518 (Year: 2014).*

Barmat, L.I. et al., "Autologous Endometrial Co-culture in Patients with Repeated Failures of Implantation After In Vitro Fertilization-Embryo Transer," Journal of Assisted Reproduction and Genetics, vol. 16, No. 3, 1999, pp. 121-127.

Barmat, L.I. et al., "Human preembryo development on autologous endometrial coculture versusconventional medium," Fertility and Sterility, vol. 70, No. 6, Dec. 1998, p. 1109-1113.

Kattal, N. et al., "Role of coculture in human in vitro fertilization: a meta-analysis," Fertility and Sterility, vol. 90, No. 4, Oct. 2008, pp. 1069-1076.

Marques et al., "Sol-gel derived nano/macroporous monolithic scaffolds," Euro. J. Glass Sci. Techno., 48 (2007) pp. 65-68.

Marques et al., "Nano/macroporous monolithic scaffolds prepared by the sol-gel method," J. Sol-Gel Sci. Techno. 51 (2009) 42-47.

Marques et al., "Sol-gel derived glass scaffold with high pore interconnectivity and enhanced bioactivity," J. Mater. Res. 24 (2009) 3495-3502.

Moawad and Jain "Fabrication of nano-macro porous soda-lime phosphosilicate bioactive glass by the melt-quench method," Developments in Porous, Biological and Geopolymer Ceramics. Proc. 30th Int. Conf. Advanced Ceramics and Composites, Cocoa Beach, FL, 2006. pp. 183-195.

Moawad and Jain, "Creation of Nano—Macro-Interconnected Porosity in a Bioactive Glass—Ceramic by the Melt-Quench-Heat-Etch Method", J. Am. Ceram. Soc. vol. 90, No. 6, 2007, pp. 1934-1936.

Moawad et al., "Development of nano-macroporous soda-lime phosphofluorosilicate bioactive glass and glass-ceramics," J. Mater. Sci.: Mater. Med. 20(7) (2009) 1409-18.

Seta "Embryo transfer after autologous endometrial coculture improves pregnancy rates," Hum Cell 2001; 14: 135-40.

Spandorfer, S.D. et al., "Granulocyte Macrophage-Colony Stimulating Factor Production by Autologous Endometrial Co-Culture Is Associated with Outcome for In Vitro Fertilization Patients with a History of Multiple Implantation Failures," American Journal of Reproductive Immunology, vol. 40, 1998, pp. 377-381.

Spandorfer, S.D. et al., "Interleukin-1 Levels in the Supernatant of Conditioned Media of Embryos Grown in Autologous Endometrial Coculture: Correlation with Outcome After In Vitro Fertilization," American Journal of Reproductive Immunology, vol. 43, 2000, pp. 6-11.

Vueva et al., "Monolithic Glass Scaffolds with Dual Porosity Prepared by Polymer-Induced Phase Separation and Sol-Gel," J. Am. Ceram. Soc. 93 [7] (2010) 1945-1949.

* cited by examiner

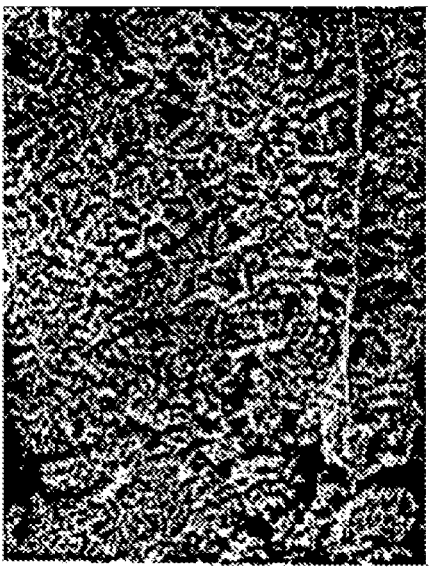
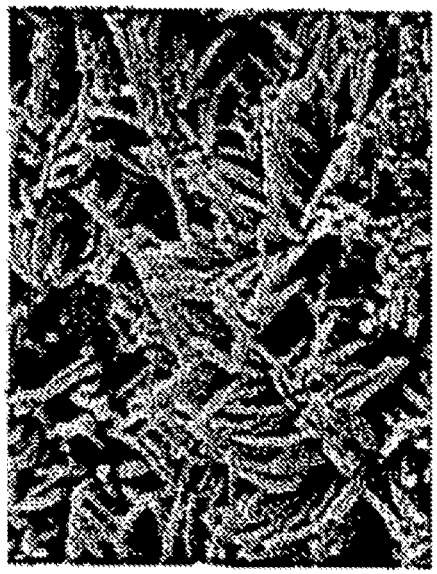
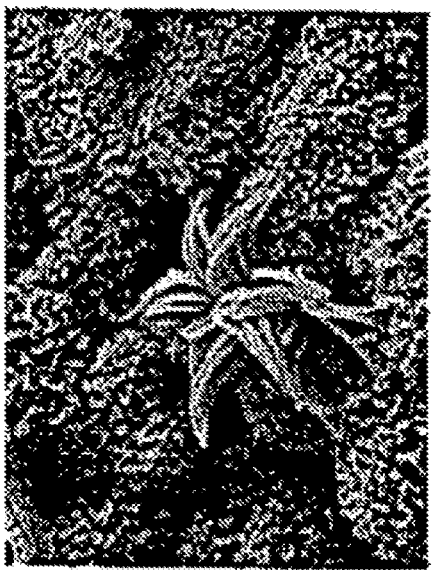
FIG. 1
FIG. 2C
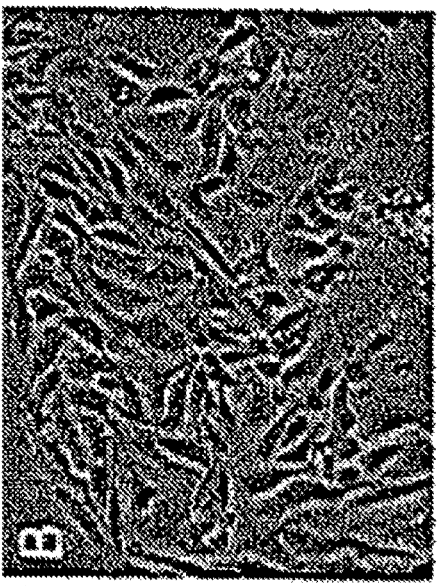
FIG. 2B
FIG. 2A

SCAFFOLDS FOR UTERINE CELL GROWTH

REFERENCE TO RELATED APPLICATION

This application is based on U.S. Provisional Application No. 62/408,407, filed Oct. 14, 2016, and is hereby incorporated by reference.

FIELD OF INVENTION

The present invention relates, generally, to scaffolds for tissue growth, and, more specifically, to scaffolds to facilitate uterine tissue growth with polarization.

BACKGROUND

In Vitro Fertilization (IVF) is an assisted reproductive technology, in which extracted eggs and sperm are manually combined in a laboratory dish to create an embryo. The embryo(s) is then transferred to the uterus of a patient.

Infertile patients are frequently faced with poor quality embryos in the IVF setting, resulting in significantly lower pregnancy rates. It is believed that the poor quality embryos are due, in large part, to the fact that the embryos in the IVF laboratory grow in plastic petri dishes supplemented with buffered media, which fails to mimic natural conditions of the womb. Recently, a technique called Autologous Endometrial Co-culture (AECC) has been developed that allows embryos to be grown on a layer of the patient's own uterine cells, which more closely mimics conditions within the womb. The use of AECC in in vitro fertilization improves embryo quality and pregnancy outcome by embryo exposure to cytokines and growth factors secreted by endometrial cells.

Although AECC may improve embryo quality and pregnancy outcomes by being exposed to uterine cell secretions and growth factors, AECC has limitations. A primary limitation is the fact that uterine cells are grown on a plastic plate, which causes them to grow flat and lose polarity. By comparison, in a normal pregnancy, the lining of the uterus (endometrium) is made of polarized cells, which initially nurtures and embeds the fertilized egg to ensure its development into a healthy fetus. More specifically, healthy endometrial epithelial cells (also referred to herein generally as uterine cells) exhibit a highly polarized morphology growing columnar, with cilia (hair-like) extensions on their apical, uterus-lumen exposed side, and a flat surface on their basal uterus muscle tissue (myometrium) oriented side as shown in FIG. 1. However, when grown in standard cell culture vessels, they lose their polarized 3-D morphology and grow attached flat on the vessel surface as shown in FIG. 2. Specifically, FIG. 2(a) shows cells grown out from a fragment of uterine endometrial tissue onto TC plastic, FIG. 2(b) shows cells exhibiting a curved, flattened morphology, and FIG. 2(c) shows several different types of cells based on differences in morphology. Thus, when cultured in standard, presently FDA-approved vessels, uterine cells lose polarization, hampering in-vitro embryo development.

The success of IVF using AECC increases significantly when fertilized eggs are cultured on a layer of uterine cells grown on a porous substrate. One such porous substrate is the Matrigel® substrate, which has been shown to support polarized growth. However, because Matrigel® substrates are organic and are of animal origin, they may carry animal-borne pathogens. Furthermore, because they are organic, they cannot undergo autoclave processing or other serialization process, and thus pose a risk of pathogen infection, and hence not approved by FDA.

What is needed is a biocompatible porous substrate that not only facilitates polarized growth of uterine cells growth, but also can be serialized to eliminate pathogens. The present invention fulfills this need among others.

SUMMARY OF INVENTION

The following description presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention relates to a substrate for growing uterine cells that not only facilitates polarization, but also can be autoclaved and undergo sterilization. Applicants have discovered that the use of silica-based scaffolds with substantial porosity facilitates the growth of uterine cells with polarization. Because the scaffolds are silica based they can be readily autoclaved and thus sterilized. Likewise, because they are inert/inorganic, there is a significantly reduced risk of diseases, and infection from viruses or other animal-borne pathogens as with prior art scaffolds. Likewise, silica-based scaffolds can be subjected to high temperatures and harsh processing conditions without degradation Accordingly, in one embodiment, the invention relates to a method for growing polarized endometrial cells, comprising (a) disposing endometrial cells on a scaffold, the scaffold comprising a silica-based glass composition, characterized by substantial porosity, the scaffold defining a top side and a bottom side, (b) providing nutrients to the top and bottom sides of the scaffold, and (c) providing an environment to grow polarized endometrial cells on the scaffold.

BRIEF DESCRIPTION OF FIGURES

FIG. 1 shows scanning electron micrographs (SEMs) of uterine epithelium (myometrium) at increasing magnification. Polarization of the epithelial cells is indicated by numerous clearly visible cilia (hair-like extensions) exposed on the apical surface (=uterus lumen).

FIG. 2A shows cells grown from a fragment of uterine endometrial tissue onto TC plastic.

FIG. 2B shows cells exhibiting a curved, flattened morphology.

FIG. 2C shows several different types of cells based on differences in morphology.

DETAILED DESCRIPTION

Figures 3A, 3B, 3C, 3D:
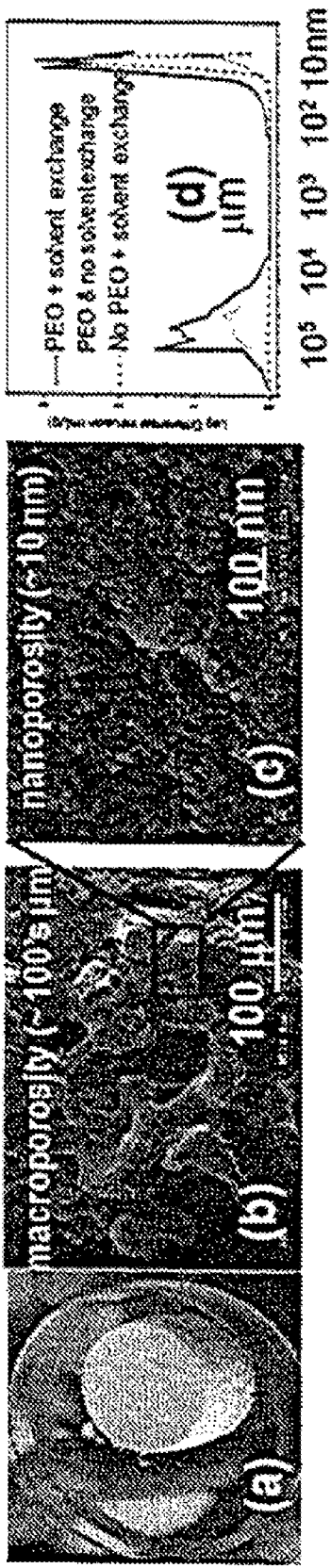
FIG. 3A shows a bulk sample of a scaffold used in the present invention.
FIG. 3B and FIG. 3C are scanning electron microscope (SEM) micrographs of the scaffold of FIG. 3A, showing coexisting interconnected macro and nano porosity
FIG. 3D shows pore size distribution of the scaffold of FIG. 3A.

In one embodiment, the invention relates to a method for growing polarized endometrial cells. The method comprises disposing endometrial cells on a scaffold, the scaffold comprising a silica-based glass composition, characterized by substantial porosity, the scaffold defining a top side and a bottom side. The method also comprises providing nutrients to the top and bottom sides of the scaffold, and providing an environment to grow polarized endometrial cells on the scaffold. These steps are considered in greater detail below with respect to selective alternative embodiments.

The scaffold should have certain characteristics. First, it needs to comprise a biocompatible, preferably bioactive, material to facilitate cell growth. Second, it needs to be capable of being sterilized to eliminate any pathogens. Although sterilization methods may differ, in one embodiment, the scaffold is capable of being sterilized using an autoclave. To this end, the scaffold should be an inorganic material, such as a silicate glass, capable of withstanding high temperatures. Suitable materials include, for example, a silicate glass of the formula: 30% CaO-70% $SiO_2$. In another embedment the composition comprises a glass of the formula: 24.5 CaO-(27.5−x)$Na_2O$-6$P_2O_5$-(42+x)SiO2 (wt %), wherein x is from about 0 to about 10, and, in one particular embodiment, x is 3. In still another embodiment, the composition comprises a silicate glass of the formula: 24.4% $Na_2O$-26.9% CaO-2.6% $P_2O_5$-46.1% SiO2 (mol %). Still other embodiments will be known or obvious to those of skill in the art in light of this disclosure.

The scaffold may be configured in different ways. For example, the scaffold may be substantially planar, or it may be curved or undulating, depending on the application. Still other embodiments will be known or obvious to those of skill in the art in light of this disclosure.

The scaffold is substantially porous to facilitate polarized uterine cell growth. Generally, although not necessarily, the scaffold has a multimodal porosity. In one embodiment, the multi-modal porosity is characterized by an interconnected microstructure of nanopores and macropores. As used herein, nanopores range in size from 5 to 100 nanometers, and macropores range in size from 1 to 300 micrometers. In one embodiment, the macropores have an average pore diameter of greater than about 10 micrometers, and in another embodiment, the nanopores have an average diameter of less than about 100 nanometers. In one embodiment the nano-macro porous calcium silicate glass scaffold samples were prepared with overall porosity varying from 38% to 77%, with accessible surface area varying between 35 and 300 $m^2/g$.

Different techniques can be used to prepare the scaffold of the present invention. For example, in one embodiment, the scaffolds are prepared by a modified sol-gel method as disclosed in U.S. Pat. Nos. 8,277,829 and 9,321,675, and several subsequent publications—i.e. (a) Sol-gel derived nano/macroporous monolithic scaffolds, A. C. Marques, H. Jain, R. M. Almeida, Euro. J. Glass Sci. Techno., 48 (2007) 65-68; (b) Ana C. Marques, Himanshu Jain, Carol Kiely, Kai Song, Chris J. Kiely and Rui M. Almeida, J. Sol-Gel Sci. Techno. 51 (2009) 42-47; (c) Sol-gel derived glass scaffold with high pore interconnectivity and enhanced bioactivity, Ana C. Marques, Rui M. Almeida, Amath Thiema, Shaojie Wang, Matthias Falk, Himanshu Jain, J. Mater. Res. 24 (2009) 3495-3502; and (d) Monolithic Glass Scaffolds with Dual Porosity Prepared by Polymer-Induced Phase Separation and Sol-Gel, Yuliya Vueva, Ana Gama, Alexandra V. Teixeira, Rui M. Almeida, Shaojie Wang, Matthias M. Falk, and Himanshu Jain, J. Am. Ceram. Soc. 93 [7] (2010) 1945-1949.

Alternatively, scaffolds can be prepared by a melt-quench-heat-etch method, as described in U.S. Pat. Nos. 8,389,018 B2, 9,656,900, and 9,701,566, and also in publications: (a) Creation of Nano-Macro-Interconnected Porosity in a Bioactive Glass-Ceramic by the Melt-Quench-Heat-Etch Method, Hassan M. M. Moawad and Himanshu Jain, J. Am. Ceram. Soc. 90 (2007) 1934-1936; (b) Fabrication of nano-macro porous soda-lime phosphosilicate bioactive glass by the melt-quench method, Hassan M. M. Moawad and Himanshu Jain, Developments in Porous, Biological and Geopolymer Ceramics. Proc. 30th Int. Conf. Advanced Ceramics and Composites, Cocoa Beach, Fla., 2006. A. Wereszczak and E. Lara-Curzio, eds. ISBN: 978-0-470-11702-6. 2007. Pp. 183-195; and (c) Development of nano-macroporous soda-lime phosphofluorosilicate bioactive glass and glass-ceramics, H. M. M. Moawad and H. Jain, J. Mater. Sci.: Mater. Med. 20(7) (2009) 1409-18]. All of the above-mentioned patents and publications are hereby incorporated by reference in their entirety.

In one particular embodiment, the scaffold is transparent or nearly transparent, or translucent to facilitate observation of the polarized uterine cells and/or embryo. Applicants recognize that the opacity of the scaffold arises from scattering of light by the pores. Macropores tend to diminish transparency more than the nanopores. Therefore, in one embodiment, to maximum transparency, the scaffold comprises mainly or only nanopores. In one embodiment, the volume of nanopores to volume of macropores is greater than 5:1, 10:1, 50:1, 100:1, or 1000:1. Alternatively, transparency can be achieved by decreasing the thickness of the scaffold, although the scaffold needs to be thick enough to facilitate handling. In one embodiment the scaffold is less than 0.3 mm thick, and, in a more particular embodiment, it has a thickness of between about 0.3 mm and about 3 mm, and, more particularly about 1 mm. In another embodiment, transparency is achieved by varying both the concentration and size of the macro pores and the thickness of the scaffold. Still other embodiments will be known or obvious to those of skill in the art in light of this disclosure.

In one embodiment, the scaffolds are thin, membrane-like sheets of bioactive glass, Tailored Amorphous Multi-Porous bioScaffolds" (TAMPs). TAMPS are fully sterilizable product not bearing the risk of transmitting disease, while facilitating the growth of uterine cells and enhancing in-vitro embryo development. For example, referring to FIGS. 3A-3C an embodiment of a TAMP for use in the present invention is shown. FIG. 3A shows a bulk sample, and FIGS. 3B AND 3C show SEM micrographs of 30 mol % CaO-70 mol % $SiO_2$ bioscaffold with coexisting interconnected macro and nano porosity, which facilitate cell adhesion, in-growth, and fluid exchange and reacquisition of three-dimensionality. FIG. 3D shows pore size distribution for different processing conditions, showing that the size of macro- and nanopores can be controlled independently, introducing the concept of TAMP scaffolds. The TAMP can be manufactured with a tailored pore configuration. For example, the material may have interconnected ~10 nm nanopores together with ten thousand times larger macropores. More importantly, the size of nano- and macropores can be tailored independently, providing the first bioactive material for which degradation rate and other useful properties can be tailored to the needs of specific patients.

Disposing or plating the uterine cells on the scaffold can be performed using known methods. For example, in one embodiment, prior to disposing endometrial cells on the scaffold, the endometrial tissue is digested using collagenase to obtain the endometrial cells. In another embedment, prior to disposing the endometrial cells on the scaffold, the scaffold is pre-incubated in phosphate-buffered saline. In one embodiment, disposing the endometrial cells on the scaffold comprises placing the scaffold in a well, and seeding it with at least 100,000 endometrial cells that were allowed to grow to confluence. Still other embodiments will be known or obvious to those of skill in the art in light of this disclosure.

Providing nutrients and environmental conditions to facilitate uterine cell growth are known. In one embodiment, nutrients are provided to both the top and bottom of the scaffold before and/or after the uterine cells are plated on it. For example, in one embodiment, providing nutrients comprises having two separated pools of culture medium, one contacting cells on their apical surface, the other contacting cells on their basal surface which is achieved by suspending the scaffold in an insert to separate the pools (similar to commercially available Transwell inserts). Uterine cells are generally grown in the presence of serum derived from the blood of the individual patient. No biological materials other than derived from the individual patient are used. Culture conditions are standard cell culture conditions consisting of 5% $CO_2$ in air, 100% humidity, 37° C.

The method may also comprise disposing a fertilized egg on the polarized endometrial cells, and implanting the fertilized egg on the polarized endometrial cells in a uterus of a mammal. In one embodiment, the mammal is a human. Techniques for these steps are well known and will not be addressed herein.

EXAMPLE 1

The below non-limiting example demonstrates the ability of a porous silica-based substrate to support polarized uterine cell growth.

Materials and Methods

Uterine tissue was obtained by random Pipelle endometrial biopsy from infertility patients (age greater than 21 years), with no history of uterine abnormalities or spontaneous abortion. Tissue was digested using collagenase, and cells were plated using previously published protocol. Upon reaching confluence, cells were cryopreserved for future use.

The scaffolds were prepared by a modified sol-gel method as disclosed in U.S. Pat. Nos. 8,277,829 and 9,321,675 B2. The scaffolds were autoclaved for sterilization.

The sterile scaffolds were pre-incubated in phosphate-buffered saline. Scaffolds and coverslips were placed in wells and each seeded with 500,000 cells that were allowed to grow to confluence. Cellular morphology was observed by immunofluorescence using Alexa 488-phalloidin to stain filamentous actin (cytoskeleton) and 4',6-diamidino-2-phenylindole (DAPI) to detect chromatin (nuclei). Primary-secondary antibody pairing was used to stain for ADP-ribosylation factor like protein 13B (ARL13B) and acetylated tubulin (cilia), as well as tubulin (centrosomes).

Results

Figures 4A, 4B, 4C:
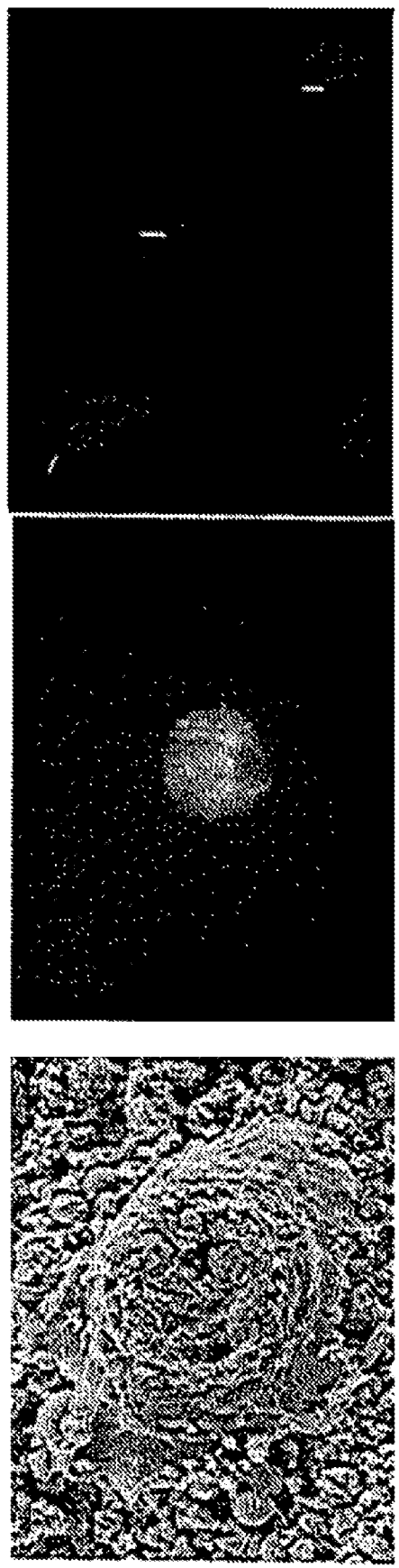
FIG. 4A shows uterine endometrial cells growing on scaffolds at a relatively high magnification level.
FIG. 4B shows the cells of FIG. 4A at a lower magnification.
FIG. 4C shows single cilia of cells, which is a marker for cell polarization.

Applicants were able to consistently and successfully grow endometrial cells on TAMP scaffolds. Staining actin demonstrates that endometrial cells growing on TAMP scaffolds have a more rounded morphology than those on coverslips, which are more elongated, exhibiting a more spindle-type morphology. With the acetylated tubulin and tubulin stains, Applicants observed single primary cilia/centrosomes on endometrial cells grown on coverslips, and Applicants have demonstrated multiple cilia paired with centrosomes on a set of cells grown on TAMP scaffolds. FIG. 4A shows uterine endometrial cells growing on TAMP scaffolds at a relatively high magnification level, and FIG. 4B shows the cells at a lower magnification. FIG. 4C shows single cilia of cells, which is a marker for cell polarization. Specifically, single cilia were detected by Arl13B staining (green), the base of cilia are detected by y-tubulin staining (red), and cell nuclei are detected by DAPI staining (blue). These examples show that Applicants can grow and detect cells on TAMPS scaffolds as shown for uterine endometrial cells. Therefore, Applicants have successfully demonstrated the growth of endometrial cells on TAMP scaffolds. Accepted morphological markers suggest that our substrate allows endometrial cells to reacquire polarity.

These and other advantages maybe realized in accordance with the specific embodiments described as well as other variations. It is to be understood that the above description is intended to be illustrative, and not restrictive. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled.

What is claimed is:

1. A method for growing polarized endometrial cells, said method comprising:
disposing endometrial cells on a scaffold, said scaffold comprising a silica-based glass composition, characterized by multi-modal porosity, said scaffold being to define a top side and a bottom side;
providing nutrients to said top and bottom sides of said scaffold and an environment to grow polarized endometrial cells on said scaffold.

2. The method of claim 1, wherein the porosity is characterized by bi-modal porosity.

3. The method of claim 2, wherein the bi-modal porosity comprises interconnected microstructure of nanopores and macropores.

4. The method of claim 3, wherein the macropores have an average pore diameter of greater than about 10 micrometers.

5. The method of claim 3, wherein the nanopores have an average diameter of less than about 100 nanometers.

6. The method of claim 1, wherein the composition comprises a glass of the formula: 30 mol % CaO-70 mol % $SiO_2$.

7. The method of claim 1, wherein the composition comprises a glass of the formula: 24.5CaO-(27.5−x)$Na_2$O-6$P_2O_5$-(42+x)$SiO_2$ (wt %), wherein x is from about 0 to about 10.

8. The method of claim 7, wherein x is about 3.

9. The method of claim 1, wherein the composition comprises a glass of the formula: 24.4% $Na_2$O-26.9% CaO-2.6% $P_2O_5$-46.1% $SiO_2$ (mol %).

10. The method of claim 1, wherein said scaffold is substantially planar.

11. The method of claim 1, wherein said scaffold is substantially flat.

12. The method of claim 1, wherein said scaffold is produced using melt-quench method of fabrication.

13. The method of claim 1, wherein said scaffold is produced using a modified sol-gel method.

14. The method of claim 1, further comprising prior to disposing endometrial cells on said scaffold, sterilizing said scaffold in an autoclave.

15. The method of claim 1, further comprising prior to disposing endometrial cells on said scaffold, digesting said endometrial tissue using collagenase to obtain said endometrial cells.

16. The method of claim 1, further comprising prior to disposing said endometrial cells on said scaffold, pre-incubating said scaffold in phosphate-buffered saline.

17. The method of claim 1, wherein disposing said endometrial cells on said scaffold comprises placing said scaffold in a well and seeding it with at least 100,000 endometrial cells grown to confluence.

18. The method of claim 1, further comprising:
disposing a fertilized egg on said polarized endometrial cells.

19. The method of claim 18, further comprising:
implanting said fertilized egg on said polarized endometrial cells in a uterus of a mammal.

20. The method of claim 19, wherein said mammal is human.

21. The method of claim 1, wherein providing nutrients to said top and bottom sides of said scaffold comprises to have two separated pools of culture medium, one contacting cells on their apical surface, and the other contacting cells on their basal surface which is achieved by suspending the scaffold in an insert to separate the pools.

* * * * *